(12) United States Patent  
Attolino et al.

(10) Patent No.: US 8,809,553 B2
(45) Date of Patent: Aug. 19, 2014

(54) PROCESS FOR THE PREPARATION OF PTERIDINE DERIVATIVES

(75) Inventors: Emanuele Attolino, Baranzate (IT); Mario Michieletti, Baranzate (IT); Davide Rossi, Baranzate (IT); Pietro Allegrini, Baranzate (IT)

(73) Assignee: Dipharma Francis S.r.l., Baranzate (MI) (IT)

( * ) Notice: Subject to any disclaimer, the term of this patent is extended or adjusted under 35 U.S.C. 154(b) by 27 days.

(21) Appl. No.: 13/703,932

(22) PCT Filed: Jun. 13, 2011

(86) PCT No.: PCT/EP2011/002896
§ 371 (c)(1),
(2), (4) Date: Dec. 13, 2012

(87) PCT Pub. No.: WO2011/157388
PCT Pub. Date: Dec. 22, 2011

(65) Prior Publication Data
US 2013/0090474 A1    Apr. 11, 2013

(30) Foreign Application Priority Data
Jun. 15, 2010 (IT) .............. MI2010A1076

(51) Int. Cl.
C07D 339/00 (2006.01)
C07D 475/04 (2006.01)
C07D 337/04 (2006.01)
C07D 339/06 (2006.01)
C07D 333/08 (2006.01)
C07H 9/00 (2006.01)
C07D 337/08 (2006.01)
C07D 339/08 (2006.01)
C07H 3/02 (2006.01)

(52) U.S. Cl.
CPC ............ *C07D 475/04* (2013.01); *C07D 337/04* (2013.01); *C07D 339/06* (2013.01); *C07D 333/08* (2013.01); *C07H 9/00* (2013.01); *C07D 337/08* (2013.01); *C07D 339/08* (2013.01); *C07H 3/02* (2013.01)
USPC ............ 549/22; 549/9; 549/29; 549/78

(58) Field of Classification Search
CPC .. C07D 339/06; C07D 339/08; C07D 337/08; C07D 333/08; C07D 333/12
USPC ............... 549/22, 9, 29, 78
See application file for complete search history.

(56) References Cited

U.S. PATENT DOCUMENTS 5,502,073 A * 3/1996 Casida et al. ............... 514/436

FOREIGN PATENT DOCUMENTS

EP    0153095 A1    8/1985
EP    1849793 A1    10/2007

OTHER PUBLICATIONS

Leung et al. Chem. Abs. DN 149:447691 (2007).*
Fragoso-Serrano M et al: "Conformational analysis of sulfur-containing 6-deoxy-L-hexose derivatives by molecular modeling and NMR spectroscopy. A theoretical study and experimental evidence of intramolecular nonbonded interactions between sulfur and oxygen", Journal of Organic Chemistry 20030919 US, vol. 68, No. 19, Sep. 19, 2003, pp. 7167-7175, XP002614859, ISSN: 0022-3263 p. 7174; compound 3 Chart 1; p. 7168; compound 3.
Greene T.W.; Wuts, P.J.: "Protective groups in organic synthesis", 1999, John Wiley and Sons, XP002614861, pp. 329-344, the whole document.
Khan, A.T.; Mondal, E.; Ghosh, S.; Islam, S.: "A simple and practical synthetic protocol for acetalisation, thioacetalisation and transthioacetalisation of carbonyl compounds under solvent-free conditions", European Journal Of Organic Chemistry, 2004, pp. 2002-2009, XP002614860, the whole document.
Taylor et al., "Pteridines. XXXVII. A Total Synthesis of L-erythro-Biopterin and Some Related 6-(Polyhydroxyalkyl) pterins", Journal of the American Chemical Society, 98:8, Apr. 14, 1976, pp. 2301-2307.

* cited by examiner

*Primary Examiner* — Andrew D Kosar
*Assistant Examiner* — Raymond Covington
(74) *Attorney, Agent, or Firm* — Rothwell, Figg, Ernst & Manbeck, P.C.

(57) ABSTRACT

The application discloses a process for the preparation of 5-deoxy-L-arabinose of formula (VI); comprising the conversion of a compound of formula (XII); wherein n is 0, 1 or 2; which can be used as intermediate for the synthesis of sapropterin.

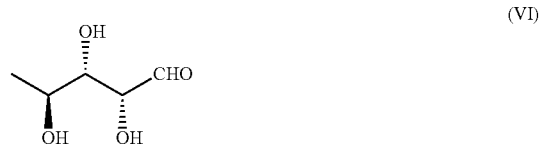

(VI)

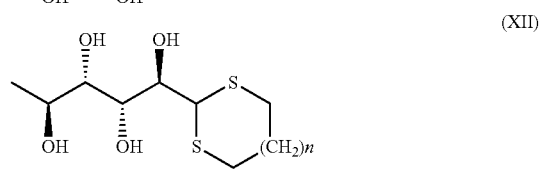

(XII)

12 Claims, No Drawings

PROCESS FOR THE PREPARATION OF PTERIDINE DERIVATIVES

CROSS REFERENCE TO RELATED APPLICATION

This application is a 35 U.S.C. 371 National Phase Entry Application from PCT/EP2011/002896, filed Jun. 13, 2011, which claims the benefit of Italian Patent Application No. MI2010A001076 filed on Jun. 15, 2010, the disclosure of which is incorporated herein in its entirety by reference.

FIELD OF THE INVENTION

The present invention relates to a novel process for the preparation of Sapropterin or a pharmaceutically acceptable salt thereof, and of novel synthetic intermediates thereof.

TECHNOLOGICAL BACKGROUND

Sapropterin, namely (6R)-2-amino-6-[(1R,2S)-1,2-dihydroxypropyl]-5,6,7,8-tetrahydro-4(1H) pteridinone, of formula (I), is the synthetic version of the 6R diastereomer of tetrahydrobiopterin (BH$_4$), the cofactor of phenylalanine hydrolase, the enzyme responsible for phenylalanine metabolism.

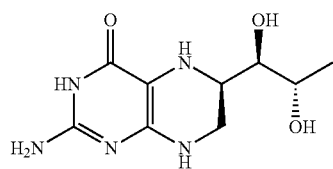

(I)

The structure has three stereogenic centers, two in the dihydroxypropyl side chain and the third at the connection between the side chain and the pteridine ring (C-6).

The absolute configuration (R) at this center is required to obtain the desired pharmacological effects, as the 6S diastereomer can even induce the inactivation of phenylalanine hydrolase, thus inhibiting the effects of the 6R diastereomer.

Sapropterin as the polymorph anhydrous dihydrochloride salt, Form B, is at present clinically used for the treatment of hyperphenylalaninaemia in patients suffering from phenylketonuria or BH4 deficiency.

Sapropterin, herein referred to also as 6R-Sapropterin, is prepared (Scheme 1) by platinum-mediated catalytic hydrogenation of Biopterin of formula (II) or of derivatives thereof in which the amine and/or hydroxy functionalities are protected with conventional protective groups Scheme 1

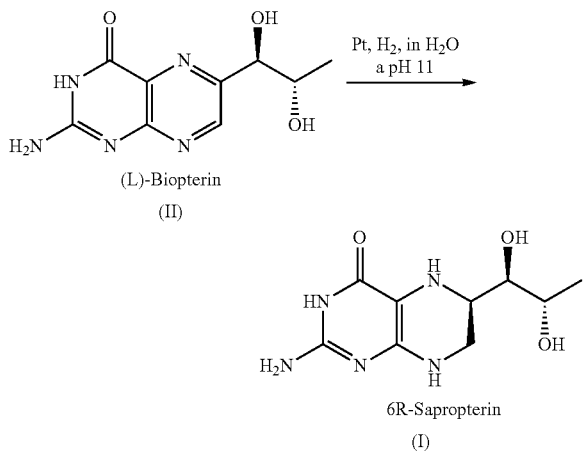

The hydrogenation reaction was reported for example in EP 0191335, which states that hydrogenation diastereoselectivity improves when the reaction is carried out in aqueous solution at basic pH under high hydrogen pressures.

Therefore, the synthetic problem for the preparation of Sapropterin is to obtain L-biopterin of formula (II) on an industrial scale with a safe, efficient process.

The synthesis of L-biopterin on an industrial scale is presently carried out starting from L-rhamnose of formula (III) (Scheme 2)

Scheme 2

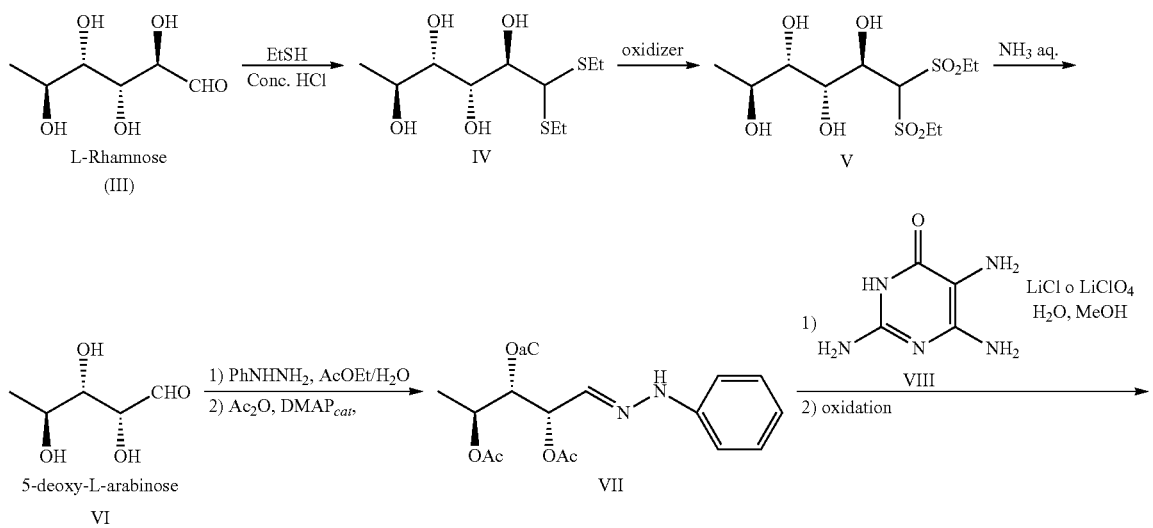

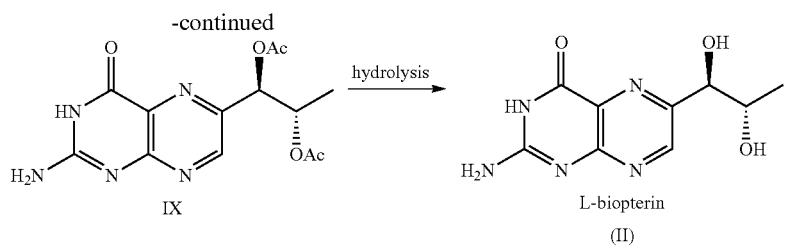

L-biopterin
(II)

This synthesis involves the transformation of L-rhamnose monohydrate of formula (III), commercially available at extremely low prices, into its diethyl dithioacetal (IV) using ethanethiol both as reagent and solvent, in the presence of concentrated hydrochloric acid. Dithioacetal of formula (IV) is then oxidized with any known oxidizers to the corresponding disulfone of formula (V), which is then subjected to MacDonald-Fischer degradation under basic conditions, to provide 5-deoxy-L-arabinose of formula (VI) bearing the hydroxy functionalities of the desired absolute configuration, in aqueous solution. The reducing sugar of formula (VI) is then converted to the corresponding acetylated phenylhydrazone of formula (VII) by treatment first with phenylhydrazine and then with acetic anhydride. The compound of formula (VII) is then condensed with 6-hydroxy-2,4,5-triaminopyrimidine of formula (VIII) or a commercially available salt thereof, to give an adduct, which is not isolated but immediately subjected to oxidation to provide the acetylated biopterin of formula (IX). Basic or acid deacetylation of compound of formula (IX) yields biopterin of formula (II), which can either be isolated or maintained in solution, to be subjected to catalytic hydrogenation to provide Sapropterin of formula (I) as reported for example in above Scheme 1.

The main problem in the development of this process on an industrial scale is the preparation of 5-deoxy-L-arabinose of formula (VI), a non-natural reducing sugar, starting from L-rhamnose diethyl dithioacetal of formula (IV). 5-Deoxy-L-arabinose of formula (VI) is indeed a key intermediate in the preparation of L-biopterin of formula (II) and therefore of Sapropterin.

Ethanethiol used in this preparation is a reagent widely known for the paramount environmental problem its use involves. Ethanethiol has low boiling point (35° C.), and due to its disgusting odor that can be perceived even in a few ppm, is nowadays no longer used on an industrial scale, even in non-environmentally conscious, non-industrialized countries.

Low molecular alkylthiols, similarly to ethanethiol, are in general toxic and because of their high volatility easily contaminate the operators and the environment.

A possible solution to the problem was apparently the process disclosed in EP 1849793, which describes the preparation of L-rhamnose didodecyl dithioacetal, in yield of 75%, using dodecanethiol as the reagent. Dodecanethiol has in fact a C12 straight alkyl chain, is an inexpensive high boiling liquid, has the typical hydrocarbon odor and does not involve remarkable environmental problems, contrary to low-boiling, short chain thiols. We repeated the above described reaction, however, even when reaction parameters such as temperature, solvent, and the like were changed, it always provided (Scheme 3) mixtures of two products, namely the desired dithioacetal of formula (X) and thioglycoside of formula (XI) in nearly equimolar ratio, which are difficult to separate due to their amphiphilic nature. Therefore, the yield in the desired dithioacetal was always less than 50%. This is probably the reason why said European application has been abandoned.

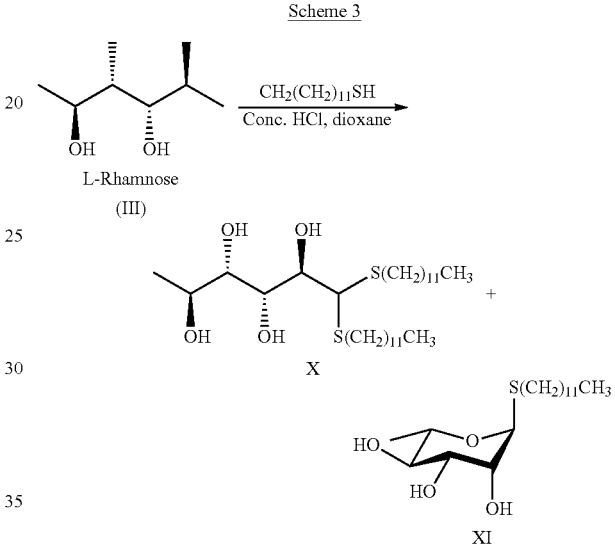

Therefore, notwithstanding the efforts carried out to date to improve the synthesis of 5-deoxy-L-arabinose of formula (VI), there is still the need for an efficient, safe process for the preparation of L-biopterin of formula (II) and then Sapropterin of formula (I), or a salt thereof, on an industrial scale.

SUMMARY OF THE INVENTION

A novel process has now been surprisingly found which provides 5-deoxy-L-arabinose of formula (VI) from a novel rhamnose dithioacetal of formula (XII), as herein defined. The novel process overcomes the above reported mentioned problems, for instance with respect to dodecanethiol, it definitely involves a better atom economy and the thioglycoside impurity of formula (XI) or analogues thereof are not formed. Moreover it allows to obtain Sapropterin, or a pharmaceutically acceptable salt thereof, in very high yields, in a safer, efficient and reproducible manner without environmental problems on an industrial scale.

DETAILED DISCLOSURE OF THE INVENTION

An object of the invention is therefore a process for the preparation of 5-deoxy-L-arabinose of formula (VI)

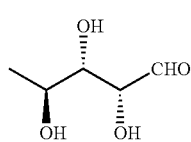

(VI)

comprising the conversion of a compound of formula (XII)

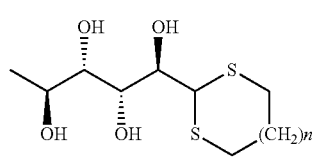

(XII)

wherein n is 0, 1 or 2;
to a compound of formula (VI) as defined above.

The conversion of dithioacetal of formula (XII) to 5-deoxy-L-arabinose of formula (VI) can be carried out by a process comprising the oxidation of a dithioacetal of formula (XII) to obtain a disulfone of formula (XIII)

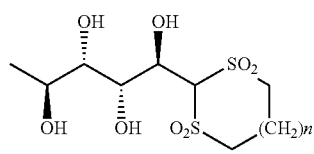

(XIII)

in which n is as defined above, and the subsequent reaction with a base.

The oxidation of a dithioacetal of formula (XII) can be carried out with an oxidizing agent for example selected from an organic peracid, preferably metachloro perbenzoic acid, periodic acid or a salt thereof, for example sodium periodate, a peroxysulfate, for example $K_2SO_5$, oxone, and hydrogen peroxide, optionally in the presence of a metal catalyst, for example sodium tungstate.

If necessary, the reaction can be carried out in a solvent, which is selected depending on the oxidizing agent, as known to those skilled in the art.

A base, which can be organic or inorganic, strong or weak, is preferably an amine, for example triethylamine or ammonia, more preferably ammonia.

According to a further aspect, the invention provides a process further comprising the conversion of 5-deoxy-L-arabinose of formula (VI), thus obtained, which can optionally be isolated, to L-biopterin of formula (II), or a salt thereof; and, if desired, the subsequent conversion of the latter to Sapropterin of formula (I) or a salt thereof.

The conversion of 5-deoxy-L-arabinose of formula (VI) to L-biopterin of formula (II), can be carried out for example according to Scheme 2 above, or according to *Helv. Chim. Acta* 1985, 68(6), 1639-1643.

The conversion of L-biopterin of formula (II), or a salt thereof, to Sapropterin of formula (I), or a salt thereof, can be carried out for example by catalytic hydrogenation according to Scheme 1 above.

A salt of L-biopterin of formula (II) or of Sapropterin of formula (I) is preferably a pharmaceutically acceptable salt thereof, for example a salt with an organic or inorganic acid, in particular with hydrochloric acid, typically the dihydrochloride. The salification of L-biopterin of formula (II) or of Sapropterin of formula (I), as well as the conversion of said salts to the respective bases, can be carried out according to known methods.

A dithioacetal of formula (XII) can be prepared by a process comprising the reaction between L-rhamnose, for example commercial, anhydrous or hydrate, with a dithiol of formula (XIV)

$$HS-(CH_2)_n-SH \quad (XIV)$$

wherein n is 0, 1 or 2, in the presence of a strong acid, and optionally in the presence of a solvent.

Dithiols of formula (XIV) are commercially available. Preferred are those in which n is 1 or 2. Such dithiols in which n is 1 or 2 have only 3 or 4 carbon atoms, like low alkyl thiols, but have higher boiling point, i.e. 169° C. or higher, moreover they do not have pungent smells in spite of their low number of carbon atoms. Thanks to this properties, in particular their low volatility, such dithiols are more suitable than other alkyldithiols for the use on an industrial scale.

A strong acid, which can be organic or inorganic, is preferably a mineral acid, for example aqueous hydrochloric acid.

A solvent, if present, can be a polar aprotic solvent, for example an amide, typically dimethylacetamide, dimethylsulfoxide or acetonitrile; a polar protic solvent, for example water or a $C_1$-$C_5$ alkanol, an ether, for example tetrahydrofuran or dioxane, or a mixture of two or more, preferably 2 or 3, of them.

The reaction can be carried out at a temperature ranging from about 0° C. to the reflux temperature of the solvent, preferably around 20° C.

Dithioacetals of formula (XII) and disulfones of formula (XIII) are novel compounds and are a further object of the invention.

According to a further aspect, the invention provides a process for the preparation of Sapropterin, or a pharmaceutically acceptable salt thereof, which comprises the use of a compound of formula (XII), as herein defined, as the starting material.

The following examples illustrate the invention.

Example 1

Synthesis of (L)-rhamnose 1',3'-propanedithioacetal (XII; n=1)

L-Rhamnose monohydrate (168.3 g, 0.92 mol) is added as a solid in portions, under strong stirring, to a mixture of 1,3-propanedithiol (100 g, 0.92 mol) in 500 ml of 37% HCl. The resulting solution is kept under stirring for 12 hours at about 20° C. Already at the first hour, formation of an abundant white precipitate is observed. The suspension is then cooled to 5-10° C. and the acid excess is neutralized with NaOH and 500 ml of ice. The suspension at pH of about 7 is then filtered and the solid is washed with water and 100 ml of isopropanol. The wet solid is dried under vacuum at 40° C. for 16 hours to attain 222 g of product (XII) as an off-white solid in 95% yield.

$C_9H_{18}O_4S_2$; MW=254.27; $^1$H-NMR (300 MHz, DMSO-d6), δ 5.05 (d, 1H, J=5.7 Hz, OH), 4.42 (d, 1H, J=1.2 Hz, H-1), 4.38 (d, 1H, J=5.4 Hz, OH), 4.22 (d, 1H, J=7.2 Hz, OH), 4.00 (d, 1H, J=8.1 Hz, OH), 3.77-3.68 (m, 2H, H-2,

H-5), 3.56-3.51 (m, 1H, H-4), 3.28-3.25 (m, 1H, H-3), 2.96-2.67 (m, 4H, 2×C$\underline{H}_2$S), 2.05-1.94 (m, 1H, SCH$_2$C$\underline{H}_a$), 1.78-1.64 (m, 1H, SCH$_2$C$\underline{H}_b$), 1.10 (d, 3H, J=6.3 Hz, CH$_3$).

Example 2

Synthesis of 1',3'-propanedisulfonyl (L)-rhamnose (XIII; n=1)

Sodium tungstate dihydrate (13 g, 0.04 mol) is suspended in a solution obtained by dissolving (L)-rhamnose-1',3'-propanedithioacetal (XII), (200 g, 0.79 mol) in 1.2 L of glacial acetic acid. The suspension is cooled to about 15° C. and 35% hydrogen peroxide (417 mL, 4.72 mol) is slowly dropped thereinto, keeping the temperature below 40° C. The resulting clear solution is stirred at about 20° C. for 16 hours. The H$_2$O$_2$ excess is then quenched by addition of a sodium thiosulfate concentrated solution. The solvent mixture is then evaporated under reduced pressure to a volume of about 400 mL. The resulting mixture is used directly in the subsequent step, without further purification.

C$_9$H$_{18}$O$_8$S$_2$; MW=318.37; $^1$H-NMR (300 MHz, DMSO-d$_6$), δ 6.24 (d, 1H, J=6.9 Hz, OH), 4.82 (d, 1H, J=7.2 Hz, OH), 4.59-4.54 (m, 2H, H-1, OH), 4.45 (d, 1H, J=5.7 Hz, OH), 4.21 (d, 1H, J=8.4 Hz, H-2), 3.63-3.24 (m, 3H, H-5, H-4, H-3), 2.44-2.14 (m, 6H), 1.12 (d, 3H, J=6.0 Hz, CH$_3$).

Example 3

Synthesis of 1',3'-propanedisulfonyl (L)-rhamnose (XIII; n=1)

(L)-Rhamnose-1',3'-propanedithioacetal (XII) (200 g; 0.738 mol) and sodium tungstate dihydrate (12.2 g, 0.037 mol) are dissolved in glacial acetic acid (991.6 g). Water (48 g) is added to the resulting solution and the reaction mixture is cooled to 10-15° C. 35% hydrogen peroxide (322.5 g; 3.32 mol) is added in at least 4 hours maintaining the temperature at 20-30° C. The reaction mixture is then heated at about 30-35° C. and maintained under stirring for about 3 hours. Isopropanol (416.7 g) is then added. The resulting suspension is maintained under stirring at 30-35° C. for about 5 hours, then cooled to 20-25° C. in at least 5 hours, subsequently cooled to a 5-10° C. in at least 3 hours and maintained under stirring for another hour. The suspension is cooled and then filtered and the resulting solid is washed with isopropanol (314.2 g).

The product is dried under vacuum at 50° C. for about 24 hours.

209.9 g of product are obtained, as a white solid of formula (XIII), in 88% molar yield.

C$_9$H$_{18}$O$_8$S$_2$; MW=318.37; $^1$H-NMR (300 MHz, DMSO-d$_6$), δ 6.24 (d, 1H, J=6.9 Hz, OH), 4.82 (d, 1H, J=7.2 Hz, OH), 4.59-4.54 (m, 2H, H-1, OH), 4.45 (d, 1H, J=5.7 Hz, OH), 4.21 (d, 1H, J=8.4 Hz, H-2), 3.63-3.24 (m, 3H, H-5, H-4, H-3), 2.44-2.14 (m, 6H), 1.12 (d, 3H, J=6.0 Hz, CH$_3$).

Example 4

Synthesis of 5-deoxy-L-arabinose (VI)

The suspension containing disulfone (XIII) from Example 2 is diluted with 1 liter of water and cooled to 10-15° C., then alkalinized to pH of 8-9 with 33% aqueous NH$_3$. A thick suspension immediately forms, which is kept under stirring for 16 hours at about 20° C., until complete disappearance of the starting product. The solid is then filtered and washed with 250 ml of water. The combined aqueous phases are extracted with ethyl acetate to remove any traces of sulfone. The resulting 5-deoxy-(L)-arabinose (VI) aqueous solution can be used as such for the subsequent reaction to obtain L-biopterin and, if desired, Sapropterin.

Example 5

Synthesis of 5-deoxy-L-arabinose (VI)

1',3'-Propanedisulfonyl (L)-rhamnose (XIII) (209.9 g; 0.650 mol) from Example 3 is dispersed in water (369.9 g) and ethyl acetate (568 g). 28% Ammonia (13.8 g) is then added till a pH higher than or equal to 8.

The reaction mixture is maintained at about 20-25° C. for 1 hour till complete disappearence of the starting product.

The end-reaction suspension is then filtered and resulting solid is washed with water (215 g). The bifase mixture obtained by filtration of the solid and containing 5-deoxy-(L)-arabinose (VI) can be used as such in the subsequent reaction to obtain L-biopterine and, if desired, Sapropterin.

The invention claimed is:

1. Process for the preparation of 5-deoxy-L-arabinose of formula (VI)

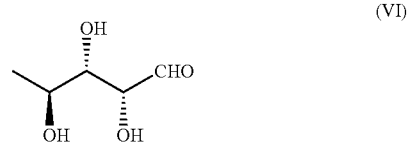

comprising the conversion of a compound of formula (XII)

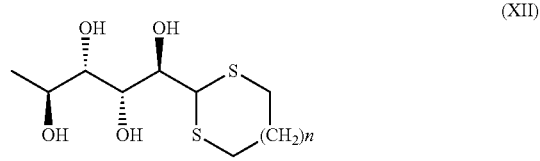

wherein n is 0, 1 or 2;
to a compound of formula (VI) as defined above.

2. Process according to claim 1, wherein the conversion of a compound of formula (XII) to a compound of formula (VI) comprises the oxidation of a dithioacetal of formula (XII) to obtain a disulfone of formula (XIII)

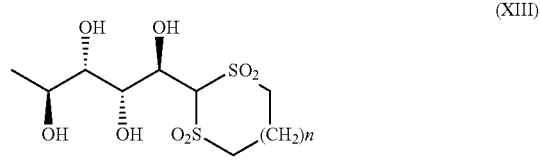

in which n is as defined in claim 1, and the subsequent reaction with a base.

3. Process according to claim 2, wherein the oxidation of a dithioacetal of formula (XII) is carried out with an oxidizing agent selected from an organic peracid, periodic acid or a salt thereof, a peroxysulfate, oxone, and hydrogen peroxide optionally in the presence of a metal catalyst, preferably sodium tungstate.

4. Process according to claim 2, wherein the base, which can be either organic or inorganic, weak or strong, is preferably an amine or ammonia.

5. Process for the preparation of L-bioterin or a salt thereof, comprising preparing 5-deoxy-L-arabinose of formula (VI)

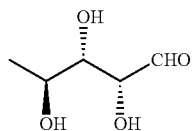
(VI)

by converting a compound of formula (XII)

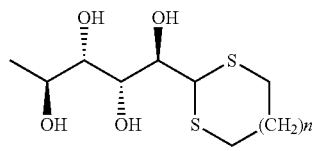
(XII)

wherein n is 0, 1 or 2;
to a compound of formula (VI) as defined above, and further comprising the conversion of said 5-deoxy-L-arabinose of formula (VI), which can be isolated or not isolated, into L-biopterin, or a salt thereof; and, if desired, its subsequent conversion into Sapropterin, or a salt thereof.

6. Process for the preparation of 5-deoxy-L-arabinose of formula (VI)

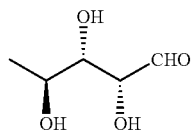
(VI)

comprising preparing a dithioacetal of formula (XII) by a process comprising the reaction of anhydrous or hydrate L-rhamnose, with a dithiol of formula (XIV)

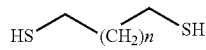
(XIV)

in which n is 0, 1 or 2, in the presence of a strong acid, and optionally a solvent, and converting said dithioacetal of formula (XII)

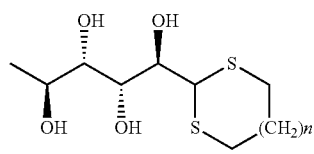
(XII)

wherein n is 0, 1 or 2;
to a compound of formula (VI) as defined above.

7. Process according to claim 6, wherein the strong acid, which can be organic or inorganic, is preferably a mineral acid.

8. Process according to claim 6, wherein the solvent is selected from a polar aprotic solvent, preferably an amide, dimethylsulfoxide or acetonitrile; a polar protic solvent, preferably water or a $C_1$-$C_5$ alkanol; an ether, preferably tetrahydrofuran or dioxane; or a mixture of two or more, preferably two or three, of said solvents.

9. A compound of formula (XII)

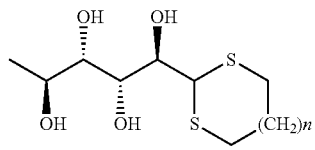
(XII)

wherein n is 1 or 2.

10. A compound of formula (XIII)

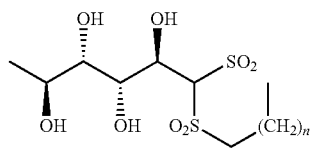
(XIII)

wherein n is 0, 1 or 2.

11. A compound according to claim 9 wherein n is 1.

12. A process for the preparation of L-biopterin or Sapropterin, or a salt thereof, comprising converting a compound of formula (XII),

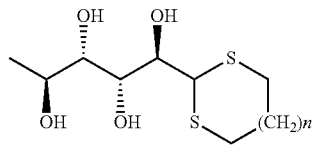

wherein n is 0, 1 or 2, into 5-deoxy-L-arabinose of formula (VI)

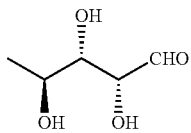
(VI)

then converting the 5-deoxy-L-arabinose of formula (VI) into L-biopterin and/or Sapropterin or a salt thereof.

* * * * *